United States Patent
Bedetti

(10) Patent No.: US 12,403,436 B2
(45) Date of Patent: Sep. 2, 2025

(54) METHOD FOR PRODUCING SOLID UREA BY GRANULATION

(71) Applicant: Casale SA, Lugano (CH)

(72) Inventor: Gianfranco Bedetti, Milan (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 17/526,759

(22) Filed: Nov. 15, 2021

(65) Prior Publication Data

US 2022/0072492 A1 Mar. 10, 2022

Related U.S. Application Data

(63) Continuation of application No. 16/819,867, filed on Mar. 16, 2020, now abandoned, which is a continuation of application No. 15/741,652, filed as application No. PCT/EP2016/063027 on Jun. 8, 2016, now abandoned.

(30) Foreign Application Priority Data

Jul. 3, 2015 (EP) ..................................... 15175347

(51) Int. Cl.
- C07C 273/14 (2006.01)
- B01J 2/16 (2006.01)
- C05C 9/00 (2006.01)
- C07C 273/16 (2006.01)

(52) U.S. Cl.
CPC ................. B01J 2/16 (2013.01); C05C 9/005 (2013.01); C07C 273/14 (2013.01); C07C 273/16 (2013.01)

(58) Field of Classification Search
None
See application file for complete search history.

(56) References Cited

U.S. PATENT DOCUMENTS

| | | |
|---|---|---|
| 2,933,526 A | 4/1960 | Guyer et al. |
| 3,398,191 A | 8/1968 | Thompson et al. |
| 4,500,336 A | 2/1985 | Van Hijfte et al. |
| 4,525,198 A | 6/1985 | Van Hijfte et al. |
| 4,842,790 A | 6/1989 | Nunnelly |
| 7,955,566 B2 | 6/2011 | Bedetti |
| 9,403,733 B2 | 8/2016 | Bedetti |
| 10,106,469 B2 | 10/2018 | Krawczyk et al. |
| 11,987,535 B2 * | 5/2024 | Marrone ............... C05G 5/37 |

(Continued)

FOREIGN PATENT DOCUMENTS

| | | |
|---|---|---|
| CN | 1878608 A | 12/2006 |
| CN | 101121618 A | 2/2008 |

(Continued)

OTHER PUBLICATIONS

Meessen ("Urea" Ullmann's Encyclopedia of Industrial Chemistry, p. 657-695, first published online on Oct. 15, 2010, and downloaded from https://onlinelibrary.wiley.com/doi/10.1002/14356007.a27_333.pub2 on Feb. 27, 2024) (Year: 2010).*

Watano ("Microgranulation of fine powders by a novel rotating fluidized bed granulator" Powder Technology, 131, 2003, p. 250-255) (Year: 2003).*

International Search Report issued on Sep. 1, 2016 in connection with PCT/EP2016/063027.

International Preliminary Report on Patentability issued on Sep. 27, 2017, in connection with PCT/EP2016/063027.

(Continued)

*Primary Examiner* — Amy C Bonaparte
(74) *Attorney, Agent, or Firm* — Akerman LLP

(57) ABSTRACT

Method for producing solid urea by granulation, wherein the granulation is fed with liquid urea having a purity greater than 98% by weight and not containing formaldehyde.

2 Claims, 2 Drawing Sheets

(56) References Cited

U.S. PATENT DOCUMENTS

| | | | |
|---|---|---|---|
| 12,103,905 B2 * | 10/2024 | Bertini | ............ C07C 273/16 |
| 2004/0143939 A1 | 7/2004 | Bedetti | |
| 2006/0177574 A1 | 8/2006 | Mutsers et al. | |
| 2007/0013092 A1 | 1/2007 | Sakata et al. | |
| 2007/0131011 A1 | 6/2007 | Bijpost et al. | |
| 2011/0064635 A1 | 3/2011 | Niehues et al. | |
| 2015/0166421 A1 | 6/2015 | Bedetti | |

FOREIGN PATENT DOCUMENTS

| | | |
|---|---|---|
| CN | 203303902 U | 11/2013 |
| RO | 111362 B1 | 9/1996 |
| RU | 2281270 C1 | 8/2006 |
| WO | 2013/189625 A1 | 12/2013 |

OTHER PUBLICATIONS

Meessen, Jozef H., "Urea", Ullmann's Encyclopedia of Industrial Chemistry, 2012, Wiley-VCH Verlag Gmbh & Co., pp. 657-695.
EPA "8.2 Urea"Emission Factors, 1995, pp. 1-6, downloaded from https:www3.epa.gov/ttn/chief/old/ap42/ch08/s02final/c08s02_jan1995.pdf.
Hicks et al., "Pilot-Plant Production of Urea-Ammonium Sulfate," Ind. Eng. Chem., Process Des. Dev., vol. 14, No. 3, 1975, pp. 269-275.
Search et al., "Source Assessment: Urea Manufacture," Environmental Protection Technology Series, Nov. 1977.
Reference Manual IFDC-R-1 "Fertilizer Manual", 1979.
"The Fisons Granular Urea Process," Nitorgen No. 98, Nov./Dec. 1975.
Reed et al., "The Spherodizer Granulation Process", Chem. Eng. Prog. 69 (1973).

* cited by examiner

METHOD FOR PRODUCING SOLID UREA BY GRANULATION

FIELD OF APPLICATION

The invention relates to the field of the production of solid urea.

PRIOR ART

Solid urea is produced mainly by prilling or granulation.

Prilling involves cooling droplets of liquid urea falling inside a tower by means of counter-flowing air. The solids thus formed are termed prills. Granulation involves spraying liquid urea onto granules inside a proper granulator, for example in a fluid bed; the liquid forms a layer which solidifies, thus increasing the size of the granule. Both techniques are known to persons skilled in the art and are described in the literature, for example in Meessen, "Urea", Ullmann's Encyclopedia of Industrial Chemistry, Wiley-VCH Verlag, 2010.

Granulation offers a series of recognized advantages and is considered to be superior to prilling. It is well-known that the prills have a certain fragility essentially due to the rapid cooling of the droplets which creates a porous structure. The solid product obtained by granulation has a much greater mechanical strength, in particular against crushing and knocks, and is therefore more suitable for storage and transportation in bulk form. Another advantage of granulation is the capacity to produce granules of a larger size, for example with a diameter of 3 mm or more, while the diameter of prills is no more than 2 mm because larger dimensions would require a too large and expensive prilling tower and would originate problems of instability of the droplets.

Despite these advantages, however, most of the solid urea is nowadays produced using the prilling technique owing to the lower cost of a prilling section compared to a granulation section.

According to the prior art and the technical literature, a prilling process requires a urea melt with a high concentration, preferably with a concentration of 99.7% by weight or more. As known, the urea plants produce (downstream of the recovery section) a solution containing a certain quantity of water (typically about 30%); hence the aforesaid concentration is reached using a suitable concentration and evaporation section designed to completely remove the water.

A granulation process, instead, according to the teaching of the prior art, is carried out with a solution of urea having a concentration of 96% or up to a maximum of 98% by weight, i.e. still containing about 2-4% of water. The granulation process is regarded as being able to tolerate a greater water content than prilling and therefore the prior art does not consider it necessary to entirely remove the water. Furthermore, a water content of around 4% is considered advantageous in the granulation process to avoid the formation of biuret which is an undesirable by-product.

The suppliers of urea technologies have developed specific granulation technologies which differ as regards certain details, but have in common the fact that they use urea with the abovementioned concentration level.

Another characteristic of the known processes-both granulation and prilling—is the addition of formaldehyde as additive for improving the mechanical characteristics of solid urea. Typically, formaldehyde is added in quantities of between 0.2% and 0.4% of the urea. The addition of formaldehyde is considered indispensable for facilitating granulation and for obtaining the mechanical strength required by the market, although it involves two drawbacks.

A first drawback is the cost: plants which produce thousands of tons of urea per day require a large quantity of formaldehyde, of the order of several tons per day, which must be provided. Formaldehyde is not always produced on site and many urea plants are located in remote areas. Providing this additive therefore gives rise to a high purchase, transportation and storage cost.

Another drawback, which is receiving an increasing attention, is the environmental impact. Solid urea (prills or granules) is mainly used in agriculture as fertilizer, which means that the formaldehyde contained in the urea is released into the ground. This creates a negative impact on the environment and problems for the human health, since formaldehyde is considered a possible carcinogen agent. But nevertheless, it is considered to be indispensable. There are procedures for producing urea without formaldehyde (called "technical urea") which, however, are costly and produce small amounts.

For the above reasons, it can be understood that there is a need to improve the quality of solid urea, in particular with reference to its purity and mechanical strength.

SUMMARY OF THE INVENTION

The idea forming the basis of the invention is to use a pure urea melt in a granulation process, without the addition of formaldehyde.

Advantageously, said urea melt has a purity of more than 98% by weight, more advantageously of at least 99.5% and even more advantageously of at least 99.7%.

The applicant has found that in conventional granulation processes the water contained in the urea feed, although in small amounts (approx. 3-4%), worsens the quality of the product. Granulation is essentially a layer-by-layer growth process and the applicant has noted that evaporation of the water (which occurs during granulation) tends to generate porosity within the core of the granule. Therefore, although the surface, i.e. the outer layer, appears to have good visual and mechanical properties, the internal layers of the granule are weakened by the porosity.

This technical problem has never been recognized in the prior art, which on the contrary encourages granulation with a urea feed of around 96% by weight. The applicant has found that a granulation process starting from substantially anhydrous urea (concentration of more than 98%) achieves a mechanical quality such that the addition of formaldehyde is no longer required. The applicant has also found that the formation of biuret nevertheless remains within the standard levels accepted by the market (for example less than 0.9%).

It should be noted that the invention requires to remove water in a more efficient way compared to conventional granulation technology, and this may result in an—albeit limited—additional cost. This cost is however offset by the superior quality of the end product and in particular by the huge advantage represented by the elimination of added formaldehyde.

The superior quality of the product arises from the improved granule structure. The invention allows obtain a more uniform granule structure owing to the elimination of the water evaporation generating porosity in the internal layers of the granule.

The elimination of the formaldehyde gives rise to dual benefit because it eliminates a costly item and a source of concern in terms of ecological and environmental impact.

The invention provides a technique for obtaining solid urea in granule form which is free from formaldehyde. The invention therefore enables urea producers to provide a product which has a mechanical strength equivalent to or superior to the granules which are nowadays available, but has the advantage of containing no formaldehyde and of being regarded as an environmentally friendly product. Formaldehyde-free urea is thus available at lower costs compared to the known processes for the production of technical urea.

An aspect of the invention is also a method for revamping existing plants with a prilling section. These plants already have an evaporation section designed to reach a high concentration (e.g. 99.7%) for correct feeding of the prilling tower, and therefore may be revamped by adding a granulation section and feeding at least part of the high-concentration urea melt, which is provided by the existing evaporation section, to the new granulation section. By doing so, the plant provides an improved product (granules instead of prills), the addition of formaldehyde can be eliminated and the already present evaporation section is exploited.

In this way the invention also responds to the need of revamping and improving the prilling tower-based urea plants, which are often outdated, but are still present in large numbers all over the world.

According to an embodiment of the invention, a part of the urea melt can be used in a prilling tower to produce seeds for the granulation process. This process is advantageous particularly when the invention is applied to the revamping of a urea plant comprising a prilling tower, since the existing prilling tower can be used for said purpose. In some embodiments the production of prills can be discontinued, which means that the output of the revamped plant is solely of granules.

The invention can be implemented using all the granulation techniques known per se. Preferably, fluid-bed granulation can be used. Even more preferably, fluid-bed granulation inside a longitudinal granulator may be used, where the fluidized granules rotate to form a vortex or two counter-rotating vortices, as explained for example in EP 1412069. Part of the urea melt feed may be suitably used to produce the seeds of the granulation process.

DESCRIPTION OF PREFERRED EMBODIMENTS

Figure 1:
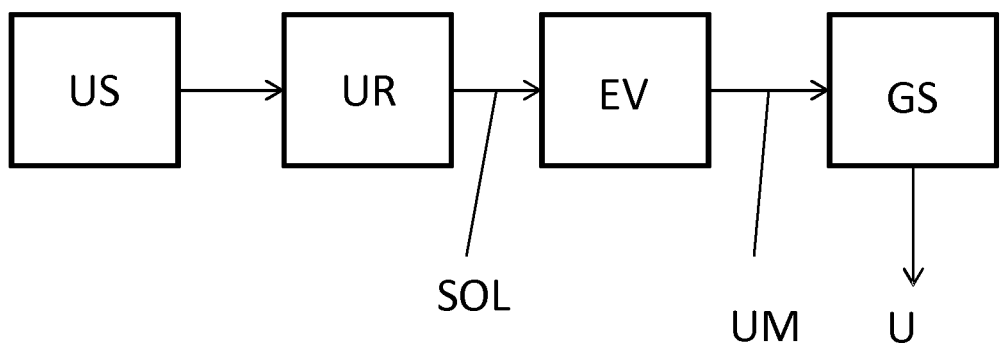
FIG. 1 is a scheme of a first embodiment of the invention.

FIG. 1 shows a schematic urea plant comprising a synthesis section US and a recycling section UR. The recycling section UR provides an aqueous solution of urea SOL containing about 70% by weight of urea.

Said solution passes through evaporation section EV inside which the water is removed, obtaining a urea melt UM containing more than 98%, for example 99.7%, by weight of urea. Said urea melt UM, without the addition of formaldehyde, is fed to a granulation section GS, obtaining granules of urea U.

Figure 2:
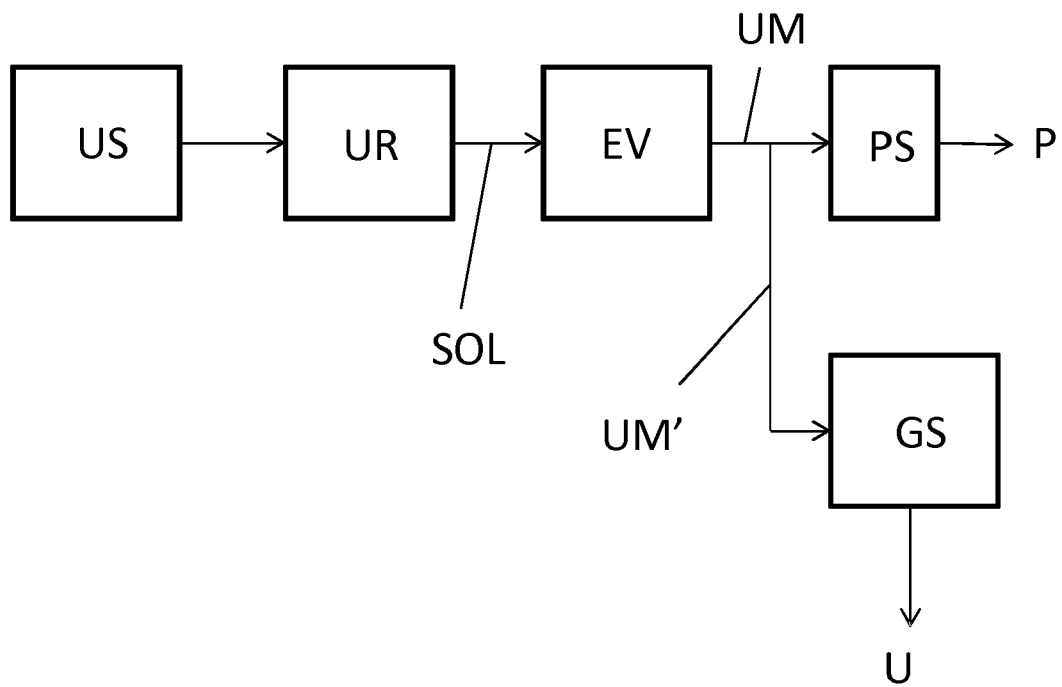
FIG. 2 is a scheme of a second embodiment.

FIG. 2 shows an example of revamping of a plant in which the urea melt UM is originally fed to a prilling section PS which produces urea prills P. At least a part UM' of said urea melt UM is fed to a granulation section GS which is arranged parallel to the prilling section PS, also in this case without the addition of formaldehyde.

In some embodiments, the UM stream is directed entirely towards the new granulation section GS, i.e. the production of prills P is discontinued.

Figure 3:
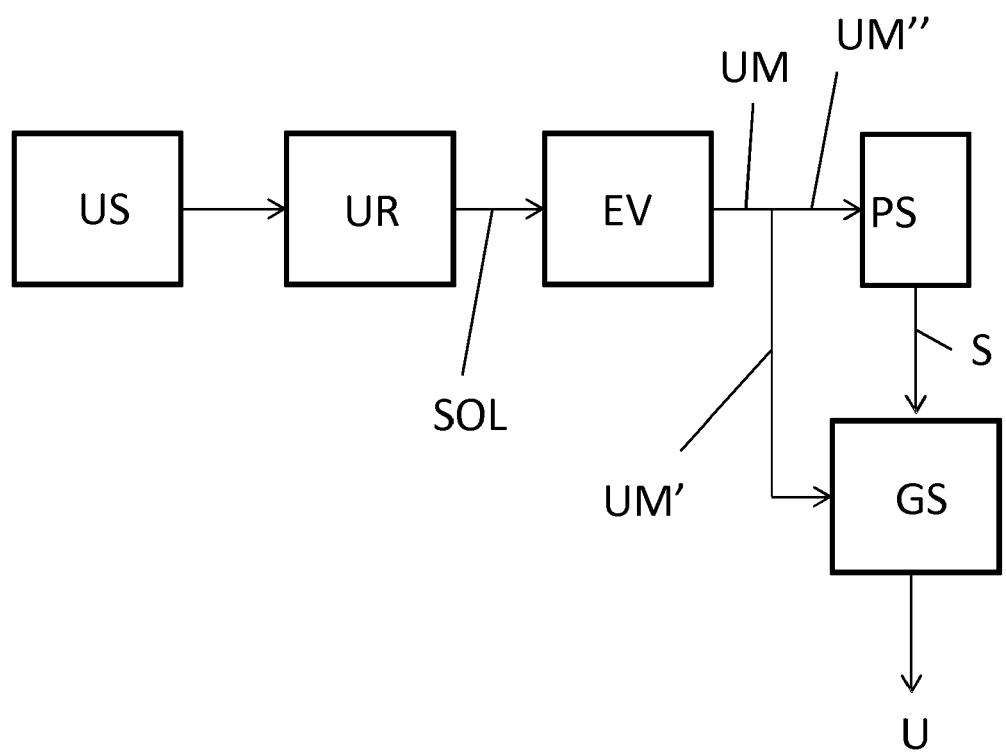
FIG. 3 is a scheme of a third embodiment.

FIG. 3 illustrates an embodiment which is a variant of FIG. 2, wherein a portion UM" of the urea melt is used in the existing prilling section PS to produce solid seeds S for the granulation section GS.

The invention claimed is:

1. A method for producing solid urea by fluid-bed granulation, the method comprising feeding the granulation with a urea melt having a concentration of at least 99.5% by weight, and wherein no formaldehyde is added to said urea melt.

2. The method according to claim 1, wherein said urea melt has a concentration of at least 99.7% by weight.

* * * * *